(12) United States Patent
Ammann

(10) Patent No.: US 6,856,930 B2
(45) Date of Patent: Feb. 15, 2005

(54) METHOD OF DETERMINING A REMAINING OPERATING TIME OF A POTENTIOMETRIC MEASURING PROBE, APPARATUS FOR PERFORMING THE METHOD, AND USE OF THE APPARATUS

(75) Inventor: Jürgen Ammann, Zurich (CH)

(73) Assignee: Mettler-Toledo GmbH, Greifensee (CH)

( * ) Notice: Subject to any disclaimer, the term of this patent is extended or adjusted under 35 U.S.C. 154(b) by 0 days.

(21) Appl. No.: 10/612,538

(22) Filed: Jul. 2, 2003

(65) Prior Publication Data

US 2004/0068385 A1 Apr. 8, 2004

Related U.S. Application Data

(63) Continuation of application No. PCT/IB01/02330, filed on Dec. 6, 2001.

(30) Foreign Application Priority Data

Jan. 5, 2001 (DE) .......................................... 101 00 239

(51) Int. Cl.⁷ ............................. G06F 19/00; G01F 1/64
(52) U.S. Cl. ..................................... 702/116; 205/789
(58) Field of Search .............................. 702/116, 176; 205/789, 777.5, 780; 600/345; 73/453

(56) References Cited

U.S. PATENT DOCUMENTS 4,189,367 A  2/1980 Connery et al.
4,686,011 A * 8/1987 Jackle ........................ 205/787.5
4,777,444 A * 10/1988 Beijk et al. ................... 324/439
4,886,584 A * 12/1989 Cheng ........................ 205/787.5
4,929,313 A * 5/1990 Wrighton .................... 205/778.5
5,139,626 A * 8/1992 Yamaguchi et al. ....... 205/778.5
5,403,451 A * 4/1995 Riviello et al. ............ 205/777.5
5,626,740 A * 5/1997 Seto et al. ..................... 205/789

FOREIGN PATENT DOCUMENTS

DE         3405431         3/1985
DE         195 10 574 C1   6/1996
DE         100 36 039 A1   2/2002
EP         0241601         10/1987
EP         0419769         4/1991

* cited by examiner

Primary Examiner—John Barlow
Assistant Examiner—Toan M. Le
(74) Attorney, Agent, or Firm—Friedrich Kueffner

(57) ABSTRACT

A potentiometric measuring probe contains an electrolyte (110) as well as a primary reference element (106) and a secondary reference element (108) that are arranged so that the front (148) of an electrolyte deficiency advancing from an opening (112) of the measuring probe arrives at the secondary reference element before it arrives at the primary reference element. The potential difference existing between the primary reference element and the secondary reference element is monitored, and when a predefined tolerance criterion is found to be violated, the elapsed operating time from the point when the measuring probe was put into operation is determined and used as a basis for calculating the remaining operating time of the measuring probe.

15 Claims, 3 Drawing Sheets

METHOD OF DETERMINING A REMAINING OPERATING TIME OF A POTENTIOMETRIC MEASURING PROBE, APPARATUS FOR PERFORMING THE METHOD, AND USE OF THE APPARATUS

This application is a continuation application of International application PCT/IB01/02330 filed Dec. 6, 2001.

BACKGROUND OF THE INVENTION

1. Technical Field

The present invention relates to a method of determining a remaining operating time of a potentiometric measuring probe containing an electrolyte as well as a primary reference element and a secondary reference element, wherein the reference elements are arranged so that an electrolyte deficiency advancing from an opening in the measuring probe arrives at the secondary reference element before it reaches the primary reference element. In addition, the scope of the invention also includes an apparatus for performing the method, as well as the use of the apparatus.

2. State of the Art

A widely used kind of measuring probe for potentiometric measurements of ion concentrations or redox potentials is equipped with a diaphragm of porous material. The diaphragm serves to bring a reference electrolyte and/or a bridge electrolyte, normally in the form of a liquid contained inside the measuring probe, into contact with a test solution. Particularly in chemical or micro-biological process-monitoring and process-control applications, the diaphragm may,be subject to contamination which can falsify the results of the measurements.

Another measuring probe, disclosed in DE 34 05 431 C2, has no diaphragm and is significantly less prone to contamination. It has a housing of an electrically insulating material with at least one enclosed space containing a reference element and an electrolyte. The housing has at least one opening through which the electrolyte can be brought into contact with a liquid solution on the outside of the housing, i.e., with the medium on which a measurement is to be performed. The enclosed space inside the housing is filled with an ion-permeable, micro-porous, high-viscosity polymer substance which, in combination with the electrolyte, forms a filler mass of the measuring probe. This type of construction assures that the electrical potential measured at the reference element is highly constant even if the solutions being measured are strongly contaminated. In addition, the measuring probe can sustain pressure levels significantly in excess of 10 bar.

Measuring probes of the foregoing description are known to have the problem that, as the cumulative operating time of the probe advances, the electrolyte that is initially contained in the polymer substance will to an increasing degree migrate into the test solution, resulting in a progressively spreading electrolyte deficiency in the polymer substance inside the housing. The increasing electrolyte deficiency in the polymer substance is also referred to as the aging process of the measuring probe and produces the undesirable effect that, when the electrolyte deficiency eventually reaches the reference element, there will be a change in the electrical potential measured at the reference element. To avoid the risk of erroneous measuring results, it is therefore necessary to monitor the aging process of the measuring probe. In particular, it should be possible to detect sufficiently in advance when the electrolyte deficiency is approaching the reference element, i.e., at a point when there is still an adequate amount of time left during which the probe can continue to operate.

According to DE 34 05 431 C2, the problem of detecting the advancement of the electrolyte deficiency can be solved by using an electrolyte consisting of a suspension of homogeneously distributed particles of a neutral salt with ions of equal transport number in an aqueous solution of the neutral salt. The polymer substance and the neutral salt suspension together form a gel that has a turbid appearance due to the salt particles in suspension. The state of aging of the measuring probe can be visually detected, as the turbidity disappears progressively with the advancement of the aging process. The reason for the decrease in turbidity is that the suspended neutral salt particles continuously pass into solution until a final state has been reached where there are essentially no suspended particles left, so that as a result the turbidity is strongly diminished. It has been found that in the aging process, a clearly visible boundary develops between a turbid portion of the gel where the neutral salt particles are homogeneously suspended and a comparatively clear portion where the neutral salt particles have passed into solution. The state of advancement of the boundary from the opening in the housing towards the reference element can be determined through visual observation. Based on a current position and speed of advancement of the boundary, it is possible to draw conclusions about the current state and speed of aging and thus predict the remaining operating time of the measuring probe.

However, the measuring probe according to DE 34 05 431 C2 has several drawbacks. To monitor the state of aging and determine the remaining operating time of the probe, it is necessary to be able to clearly see inside the enclosed space of the measuring probe. This precludes the use of a non-transparent material for the housing, and it also presents a problem with a transparent housing if the latter becomes contaminated by surface deposits. A further severe problem occurs if the gel in the enclosed space becomes discolored or contaminated, e.g., by the infusion of colored substances or infiltration of dirt particles from the test solution, which could make it practically impossible to visually detect the boundary of the electrolyte deficiency. It also has to be counted as a drawback that, in order to make the boundary visible, the electrolyte needs to be a suspension of homogeneously distributed particles of a neutral salt with ions of equal transport number in an aqueous solution of the neutral salt, a condition that excludes other kinds of electrolytes from being used in the measuring probe.

OBJECT AND SUMMARY OF THE INVENTION

The object of the present invention is to propose an improved method of determining the remaining operating time which is free of the disadvantages named above. Further objects of the invention are to provide an apparatus for performing the method, and to propose a use for the apparatus.

The first of the foregoing objectives is achieved by the method of the present invention, which serves to determine how much operating time is left in a measuring probe containing an electrolyte as well as a primary reference element and a secondary reference element, wherein the reference elements are arranged so that an electrolyte deficiency advancing from an opening in the measuring probe arrives at the secondary reference element before it reaches the primary reference element. Under the inventive method, the difference between the respective electrical potentials of the primary reference element and the secondary reference element is monitored against a predefined tolerance criterion. When the result of the monitoring ceases to meet the tolerance criterion, the elapsed operating time is determined from the point when the probe was put into operation and used as a basis for the calculation of the remaining operating time.

With the inventive method, the enclosed space in the measuring probe does not need to be accessible to visual observation. Consequently, the method can also be used in particular for measuring probes with a non-transparent housing, or for measuring probes that are installed in a probe-holder assembly. In addition, the method can also be used in measuring probes where the probe housing is covered with contaminants, as may be the case if the measuring probe is used for dirty or foamy sample solutions. Also, as the boundary of the electrolyte deficient region no longer needs to be visible, the range of applications for the inventive method is further expanded because the choice for the electrolyte is not limited by the requirement to use a suspension of homogeneously distributed particles of a neutral salt with ions of equal transport number in an aqueous solution of the neutral salt. In particular, the inventive method can also be used for measuring probes with an electrolyte consisting of a saturated or near-saturated solution of a neutral salt in an appropriate solvent, e.g., a near-saturated solution of potassium chloride in water. With the concept of determining the elapsed operating time from the point when the probe was put into operation to the point where the tolerance criterion ceases to be met and using the elapsed operating time as a basis for calculating the remaining operating time, the speed of aging of the measuring probe under the actually used operating conditions is taken into account, which leads to a more reliable prediction of the remaining operating time.

The apparatus according to the invention includes a potentiometric measuring probe with an electrolyte as well as a primary reference element and a secondary reference element, wherein the reference elements are arranged so that an electrolyte deficiency advancing from an opening in the measuring probe arrives at the secondary reference element before it reaches the primary reference element. The apparatus further includes means for determining the elapsed operating time from the point when the measuring probe was taken into operation, means for monitoring the difference between the electrical potentials of the primary reference element and the secondary reference element, and means for calculating the remaining operating time of the measuring probe. The result of the calculation can be shown in a display device and/or processed further through conventional means.

The apparatus according to the invention can be used advantageously in process-monitoring and/or process-control applications.

According to an advantageous embodiment of the invention, a detected violation of the tolerance criterion triggers a warning signal. The warning signal can for example take the form of an optical and/or acoustical indication, particularly a message that appropriate steps should be planned, such as servicing or replacement of the measuring probe.

A further embodiment of the inventive method requires a substantially continuous monitoring of the electrical potential difference. As an alternative possibility, the potential difference can be monitored at intermittent time intervals, for example periodically.

A further developed version of the inventive method includes signal-filtering in the monitoring of the electrical potential difference. This is particularly advantageous if the potential difference as a function of time is subject to fluctuations and noise.

In principle, there are several different possibilities to set a tolerance criterion or to formulate a definition as to what should be counted as a violation of the tolerance criterion. According to a first definition, a violation of the tolerance criterion occurs at the moment where the absolute amount of the potential difference leaves a predetermined tolerance range. Under another definition, violations of the tolerance criterion are defined as events where the absolute value of the first time derivative of the potential difference traverses one or more predefined tolerance values. This implies that the potential difference is monitored as a function of time. As a further possibility, violations of the tolerance criterion can be defined as events where the absolute value of the second time derivative of the potential difference traverses one or more predefined tolerance values.

In principle, there are several ways to calculate the remaining operating time of the measuring probe by using a base time period representing the amount of operating time elapsed from the point when the measuring probe was taken into operation to the time of the violation of the tolerance criterion. As an example, the remaining operating time can be calculated by multiplying the base time period with a predefined factor. Under a further advantageous concept of the invention, after detecting a violation of the tolerance criterion, the potential difference is monitored against a predefined alarm criterion, and subsequent to a violation of the alarm criterion the remaining operating time is set to zero. As an additional advantageous feature, a violation of the alarm criterion triggers an alarm signal. The embodiments that include an alarm criterion provide an additional measure of operating safety, particularly against the risk of continuing to use the measuring probe after the electrolyte deficiency has already reached the primary reference element, which could happen in a case where an indication of the remaining operating time was not noticed or was disregarded.

The concepts described above for the tolerance criterion and for defining what constitutes a violation of the tolerance criterion are analogously applicable to the alarm criterion.

BRIEF DESCRIPTION OF THE DRAWINGS

A detailed description of embodiments of the invention will be presented further below with references to the drawings, wherein.

DETAILED DESCRIPTION OF PREFERRED EMBODIMENTS

Figure 1:
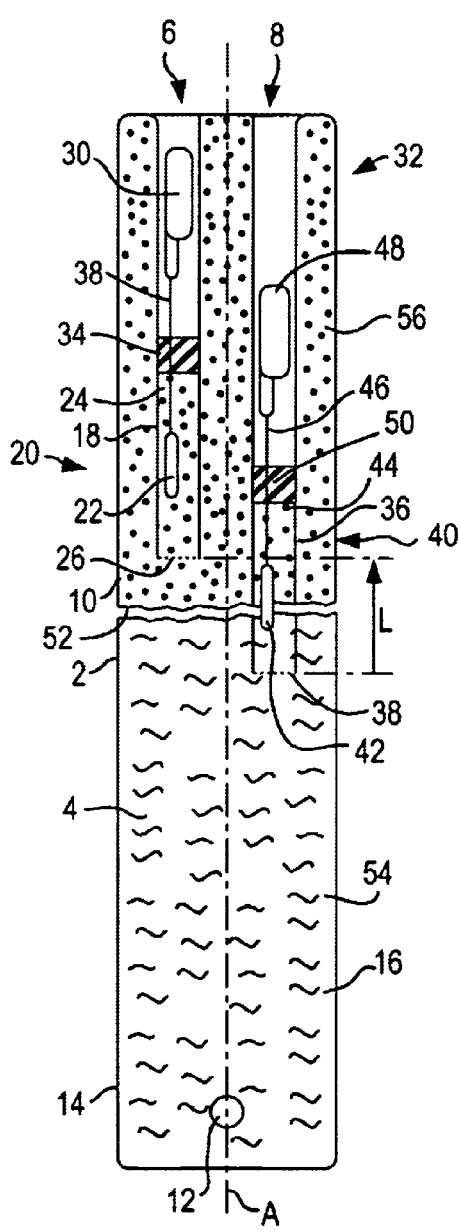
FIG. 1 represents a lengthwise sectional view of a measuring probe that is configured as a reference electrode.

FIG. 1 illustrates a measuring probe configured as a reference electrode with a tubular housing 2, usually referred to as the electrode shaft and consisting of an electrically insulating material, e.g., glass or a polymer material such as a polyarylether ketone (PAEK), in particular a polyetherether ketone (PEEK). The housing 2 surrounds an enclosed space 4 containing a primary reference element 6, a secondary reference element 8, as well as an electrolyte 10. The housing 2 has an opening 12, so that when the measuring probe is dipped into a sample solution (not shown), the electrolyte 10 is brought into contact with the sample solution. In the illustrated example, the opening 12 is formed as a passage hole in an end portion 14 of the housing 2. The enclosed space 4 is filled with an ion-permeable, high-viscosity, micro-porous polymer material which, in combination with the electrolyte 10, forms a filler mass 16. To prevent the filler mass 16 from running out of the housing through the opening 12, the filler mass should be in a highly viscous or even solid state at the normal operating temperature range of the measuring probe. As a polymer filler mass to meet this criterion, a copolymer of acrylamide and $N,N^1$-methylene-bis-acrylamide has been tried and proven.

The primary reference element 6 is configured as a cartridge 18 that is open on one side and contains a primary electrode 20 of a known potential. For example, the primary electrode is configured as an Ag/AgCl electrode with a chlorided silver wire 22 that is immersed in a primary electrolyte 24. To prevent the primary electrolyte 24 from running out of the open end 26 of the cartridge 18, the primary electrolyte 24 is enclosed in the pores of an ion-permeable, micro-porous polymer substance, preferably the same material as in the filler mass 16. On the far side from the open end 26, the primary reference element 6 has a plug-in contact 30 that communicates with the primary electrode 20 through a conductor lead 28, e.g., a platinum wire. The plug-in contact 30 serves to establish a connection to circuit elements contained in the header 32 of the measuring probe or outside of the housing. In addition, the primary reference element 6 contains a sealing plug 34, e.g., of glass or a polymer material, to prevent the plug-in contact 30 from touching the primary electrolyte 24. Instead of having an opening 26 at the end of the cartridge 18, the primary reference element 6 could have a lateral opening if desired.

The measuring probe illustrated in FIG. 1 as an example of the invention has a secondary reference element 8 that is substantially identical to the primary reference element 6. Thus, the secondary reference element 8 has a cartridge 36 with an open end 38 and a secondary electrode 40 configured as an Ag/AgCl electrode with a chlorided silver wire that is immersed in a secondary electrolyte 44. The secondary electrolyte 44 is enclosed in the pores of an ion-permeable, micro-porous polymer substance, preferably the same polymer material as in the filler mass 16. In addition, the secondary reference element 8 has a plug-in contact 48 that communicates with the secondary electrode 40 through a conductor 46, e.g., a platinum wire. The plug-in contact 48 serves to establish a connection to circuit elements contained in the header 32 of the measuring probe or outside of the housing 2. In addition, the secondary reference element 8 contains a sealing plug 50, e.g., of glass or a polymer material, to prevent the plug-in contact 48 from touching the secondary electrolyte 44.

As may be seen in FIG. 1, the primary reference element 6 and the secondary reference element 8 are positioned in the measuring probe at parallel but staggered positions, with the open end 26 of the primary reference element 6 being farther removed from the opening 12 than the open end 38 of the secondary reference element 8. As will be discussed below in further detail, the staggered arrangement has the effect that the advancing frontal boundary 52 of an electrolyte-deficient region 54 will reach the secondary reference element 8 before it reaches the primary reference element 6.

As a preferred choice, the electrolyte 10, the primary electrolyte 24, and the secondary electrolyte 44 contain a suspension of micro-particulate potassium chloride in an aqueous solution of potassium chloride. The proportion of suspended potassium chloride should be at least 30% and may be as high as 1500% in relation to the dry weight of the polymer substance. A preferred range is between 100% and 800%, with 200% to 400% being most preferred. Instead of an aqueous solution, it is also possible to use a part-aqueous solution of potassium chloride, for example a solution of potassium chloride in a mixture of water and glycerin or ethylene glycol. This has the effect of reducing the partial vapor pressure of the water, which is desirable especially in applications at elevated temperatures. Alternatively, the electrolyte 10 and/or the primary electrolyte 24 and/or the secondary electrolyte 44 could form a solid-phase electrolyte together with the polymer substance.

As the state of aging of the measuring probe progresses with the increase in accumulated operating time, an increasing portion of the electrolyte 10, i.e., of the potassium- and chloride ions initially contained in the filler mass 16, migrates into the sample solution. As a consequence, an electrolyte-deficient region 54 develops in the enclosed space 4, with a frontal boundary surface 52 of the region 54 advancing in the direction from the opening 12 towards the interior of the measuring probe. The boundary 52 represents the border between the electrolyte-deficient region 54 of the filler mass 16 in which all suspended potassium chloride particles have been dissolved and a non-deficient region 56 that still contains potassium chloride particles.

Instead of a suspension of KCl particles, one could also use a near-saturated solution of, e.g., approximately 3-molar concentration of potassium chloride in water. However, this has the disadvantage that the measuring probe will have a shorter operating time, because the initial amount of potassium chloride distributed in the filler mass 16 will be smaller than with an electrolyte in suspension form.

In the example of FIG. 1, the frontal boundary 52 of the electrolyte deficient region advances substantially along the lengthwise axis A of the housing 2. After the boundary 52 has reached and already passed the open end 38 of the secondary reference element 8, as illustrated in FIG. 1, the interior of the secondary reference element 8 will become deficient in secondary electrolyte 44. This will cause a change in the previously constant potential $V_2$ of the secondary electrode 40. With a continued use of the measuring probe, the boundary 52 would advance to the primary reference element 6, where it would cause a change of the potential $V_1$ of the primary electrode 20.

Figure 2:
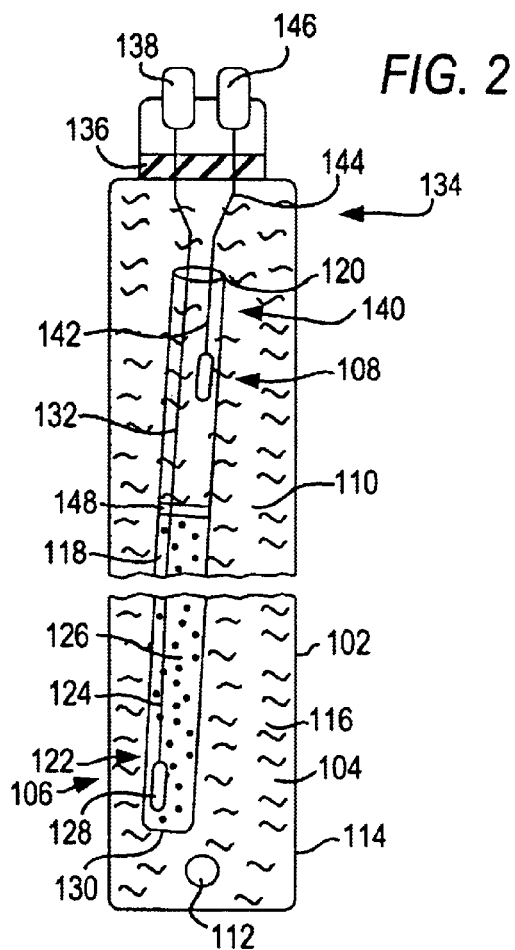
FIG. 2 represents a lengthwise sectional view, shortened by cutting out the mid-portion, of a measuring probe with a lengthened path of advancement of the electrolyte deficiency.

FIG. 2 illustrates a measuring probe in which the path for the advancement of the frontal boundary of the electrolyte deficiency has been made significantly longer. The measuring probe has a tubular housing 102 of an electrically insulating material, for example glass or a polymer material such as a polyarylether ketone (PAEK), in particular a polyether-ether ketone (PEEK). An enclosed space 104 in the housing 102 contains a primary reference element 106, a secondary reference element 108, as well as an electrolyte 110. An end portion 114 of the housing 102 has an opening 112. The enclosed space 104 is filled with an ion-permeable, high-viscosity, micro-porous polymer substance that forms a filler mass 116 together with the electrolyte 110. Preferably, the filler mass 116 is of the same composition as in the example of FIG. 1.

As illustrated in FIG. 2, the primary reference element 106 is configured as a cartridge with an interior tube 118 that runs substantially parallel to the housing 102 and is open at one end, oriented so that the open end 120 of the interior tube 118 faces in the opposite direction from the opening 112 of the measuring probe housing 102. The primary reference element contains a primary electrode 122 with a known electrode potential. In the illustrated example, the primary electrode is an Ag/AgCl electrode with a silver wire 124 that is chlorided at the end and immersed in a primary electrolyte 126. To prevent the primary electrolyte 126 from running out of the open end 120 of the interior tube 118, the electrolyte is enclosed in the pores of an ion-permeable, micro-porous polymer substance, preferably the same as in the filler mass 116. The chlorided end portion 128 of the silver wire 124 is arranged advantageously in the proximity of the closed end 130 of the interior tube 118. A wire lead 132, e.g. a platinum wire, connects the silver wire 124 to an external plug-in contact 138 by way of a seal 136, for example a glass or plastic seal, in the header part 134 of the housing 102.

The secondary reference element 108 is arranged near the open end of the interior tube 118 and has a secondary electrode 140 with a silver wire 142 that is chlorided at its end portion. The chlorided silver wire is immersed in a part of the primary electrolyte 126 that is near the open end 120 of the interior tube 118. Thus, the primary electrolyte in this case also serves as secondary electrolyte. The secondary electrode 140 is connected to an external plug-in contact 146 by a wire lead 144 running through the seal 136 in the header part 134 of the housing 102.

In the example of FIG. 2, the electrolyte-deficient region advances from the opening 112 along a path that first leads upward to the open end of the interior tube 118, then turns into the downward direction and continues all the way through the interior tube into the area near the closed end 130. FIG. 2 illustrates a situation where the frontal boundary 148 of the electrolyte-deficient portion has already progressed to the inside of the interior tube 118.

Figure 3:
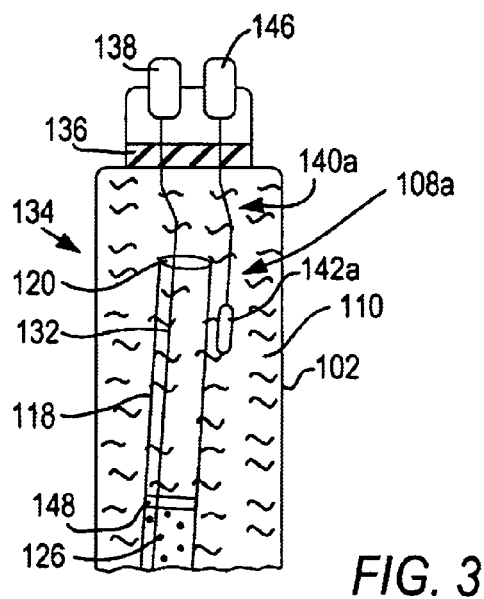
FIG. 3 represents a lengthwise sectional view of the upper part of a further measuring probe with a lengthened path of advancement of the electrolyte deficiency.

As an alternative to the foregoing arrangement, FIG. 3 illustrates a configuration where the secondary electrode 140a is arranged outside of the cartridge tube 118. Preferably, the silver wire 142a with the chlorided end portion is immersed in a part of the electrolyte 110 immediately outside the open end 120 of the interior tube 118.

In place of the wire electrodes shown in the drawing figures, one could use electrodes in the form of conductive tracks, a concept that is known per se. In any one of the foregoing embodiments, such tracks could be deposited on the inner or outer wall surface of a cartridge-shaped reference element or on the inside wall surface of the probe housing.

In addition to the foregoing embodiments, which are designed for the measurement of ion concentrations or redox potentials, it is also possible to incorporate the inventive measuring probe in a single-rod measuring chain. In this case, a measuring electrode, e.g., a pH electrode, needs to be added to the measuring probe. As a preferred configuration, the measuring electrode is arranged as a central tube running lengthwise inside a ring-shaped reference electrode as shown, e.g., in FIG. 4 of DE 34 05 431 C2.

Under the inventive method, the remaining operating time of the measuring probe of FIG. 2 is determined in accordance with the immediately following description. The method is applicable analogously to other measuring probes of the same general type.

In working with the measuring probe, the primary reference element 106 is used in a conventional manner to perform a potentiometric measurement according to a given procedure, for example in a process-monitoring and/or process-control application. The potential $V_1$ of the primary electrode 122, since it serves as the reference potential for the measurement, should be as constant as possible. However, this condition is no longer met when the frontal boundary surface 148 of the electrolyte-deficient region has arrived at the primary electrode 122. In order to provide sufficient advance warning of this undesirable event, the invention proposes the concept of monitoring the potential $V_2$ of the secondary electrode 140 or, more specifically, of the potential difference $V_{12}=V_1-V_2$. The monitoring of $V_{12}$ can be performed continuously or at intermittent time intervals, for example periodically.

Figure 4:
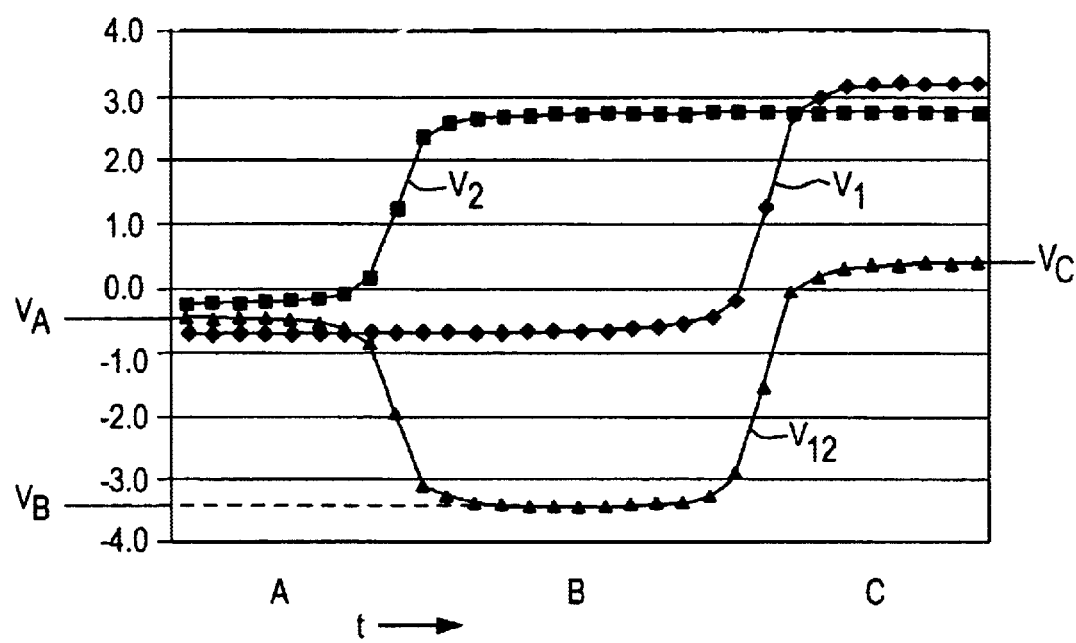
FIG. 4 represents an example for the potentials of the two reference elements as well as the potential difference as functions of the elapsed operating time.

FIG. 4 illustrates an example for the potentials $V_1$ and $V_2$ as well as the potential difference $V_{12}$ as functions of the elapsed operating time t of the measuring probe of FIG. 2. The graphs show a pattern of three distinctive time segments A, B and C, which can be explained as follows.

Following the time t=0 when the new or regenerated measuring probe has been put into operation, the deficiency boundary 148 is located in the immediate vicinity of the opening 112. If the primary electrode 122 and the secondary electrode 140 are of a substantially identical configuration, their respective potentials $V_1$ and $V_2$ will be approximately equal and the potential difference $V_{12}$ will be negligibly small. In practice however, at least a small difference $V_{12}$ will exist already at the beginning because of certain differences between the primary electrode and the secondary electrode. In the example of FIG. 4, both $V_1$ and $V_2$ are initially negative, and the potential difference $V_{12}$ has a negative value $V_A$. As long as the deficiency boundary 148 is located in the area between the opening 112 and the secondary electrode 140, the potentials $V_1$ and $V_2$ as well as the potential difference $V_{12}$ remain substantially constant. This situation is characteristic of the time segment A in FIG. 4.

After a certain length of operation of the probe, as the deficiency boundary approaches the secondary electrode 140, the potential $V_2$ of the secondary electrode begins to change and then takes on a new, substantially constant value after the deficiency boundary has passed beyond the secondary electrode. In the example of FIG. 4, the new value of $V_2$ is positive. At the same time, the potential difference $V_{12}$ goes through a first step-like transition from the initial value $V_A$ to a new value $V_B$. During the subsequent time interval B, the potential difference $V_{12}$ remains substantially constant. The deficiency boundary 148 is located in the area between the secondary electrode 140 and the primary electrode 122 during this time interval. This corresponds to the situation shown in FIG. 2.

When the deficiency boundary 148 reaches the primary electrode 122, a change occurs in the potential $V_1$. In the illustrated example, the change has the form of a step-like increase. As a consequence, the potential difference $V_{12}$ undergoes a corresponding change which, in the example of FIG. 4, manifests itself as a second step-like transition from the value $V_B$ to the value $V_C$.

As can be concluded from the foregoing example, the first step change in the potential difference $V_{12}$ indicates that the deficiency boundary has reached the secondary electrode and can thus serve as an advance warning for the impending undesirable change of the primary electrode potential. The advance warning occurs with an advance warning time substantially equal to the time interval B. The time interval B depends on the one hand on the distance L by which the two reference elements are offset from each other and on the other hand on the speed at which the deficiency boundary advances. The speed of advancement, in turn, depends on material properties and on the operating conditions of the measuring probe.

In the operation of the measuring probe, the potential difference $V_{12}$ is monitored against a predefined tolerance criterion. When the potential difference $V_{12}$ ceases to meet the tolerance criterion, a base time period $t_G$ is determined as the elapsed operating time from the point when the probe was put into operation. In accordance with its purpose, the tolerance criterion is set so that the violation of the criterion occurs approximately at the time when the front of the electrolyte-deficient region arrives at the secondary electrode. With regard to the example of FIG. 4, the tolerance criterion would thus be set so that the violation of the criterion occurs in the area of the first step change of the potential difference $V_{12}$. After the base time length $t_G$ has been determined, the remaining operating time $\Delta t_R$ of the measuring probe is calculated as a function of the base time length. Consistent with the inventive concept, the calculation is designed so that at the end of the remaining operating time $\Delta t_R$, i.e., at the time $t_A = t_G + \Delta t_R$, the front of the electrolyte-deficient region has not yet advanced to the primary reference element, i.e., the undesirable change of the potential $V_1$ has not yet occurred. Thus, in regard to the example of FIG. 4, the remaining operating time $\Delta t_R$ should definitely not be longer than the time interval B.

To ensure that the measuring probe works in a reliable manner, appropriate steps such as replacing the probe or regenerating the filler mass should be taken after the end of the base time period and in no event later than the end of the remaining operating time $\Delta t_R$. As a preferred feature, the violation of the tolerance criterion triggers a warning signal, for example in the form of an optical and/or acoustical indication that servicing measures are required. It is particularly advantageous if the remaining operating time is indicated together with the warning signal, so that a currently running process can be completed according to plan before the servicing measures are initiated.

The following discussion leads to advantageous operational definitions of the tolerance criterion and to procedures for calculating the remaining operating time. The definitions are based, among other factors, on monitoring certain quantities over time. Although these time-dependent quantities will in the following context be discussed as continuous functions, the conclusions apply analogously to functions whose values are determined at discrete individual points. In particular the term "time derivative" in the sense of a differential quotient as used below in reference to continuous functions should be understood as difference quotient when referring to discretely tabulated functions. An analogous understanding of the terms applies to signal-smoothing and signal-filtering processes.

Figure 5:
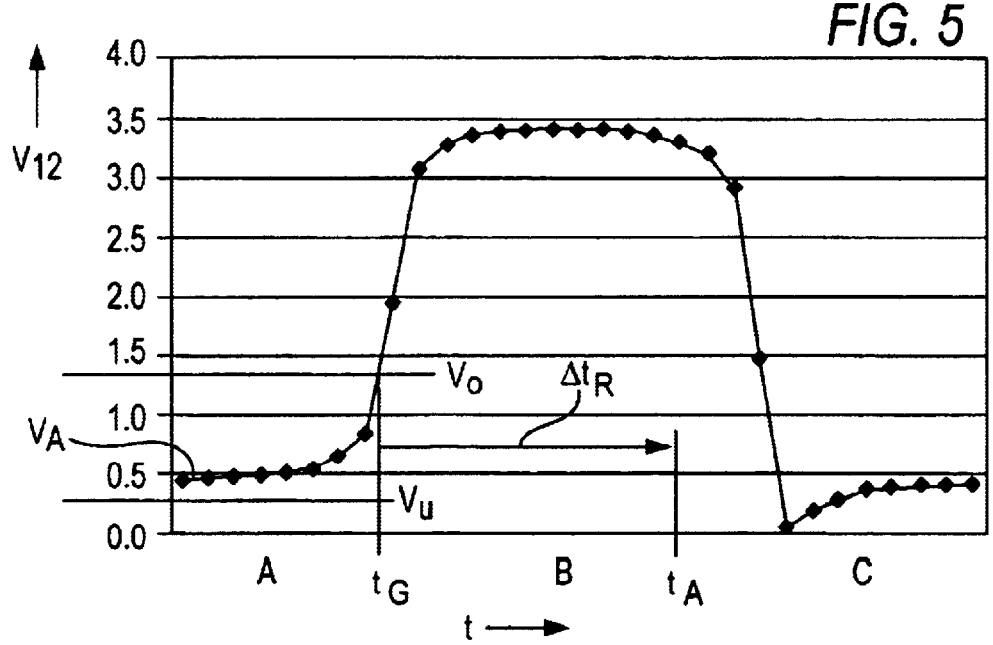
FIG. 5 represents the absolute amount of the potential difference of FIG. 4 as a function of the elapsed operating time.

In principle, the violation of the tolerance criterion could be defined as the point at which the potential difference $V_{12}$ passes above or below a predefined tolerance value. However, it needs to be taken into account that the potential difference can at the outset be positive or negative, depending on the respective types and individual characteristics of the primary and secondary electrode. Furthermore, the first step change of the potential difference can lead to positive or negative values, and the absolute amount $|V_{12}|$ of the potential difference can increase or decrease. It is therefore appropriate to use the departure of the absolute amount $|V_{12}|$ from a predefined tolerance range as a monitoring criterion. In principle, the tolerance range can be defined through predetermined values of an upper tolerance limit $V_o$ and a lower tolerance limit $V_u$. As an alternative, the tolerance range is matched to the initial value of the absolute amount $|V_{12}|$ of the potential difference. In the example of FIG. 5, the tolerance range is defined as a tolerance band that is centered on the initial value $|V_A|$ of the absolute amount $|V_{12}|$. The base time period $t_G$ is determined as the elapsed operating time up to the point at which $|V_{12}|$ runs outside the tolerance range. In the case of FIG. 5, this is where $|V_{12}|$ traverses the upper tolerance limit $V_o$. However, it needs to be emphasized that the arrival of the deficiency boundary at the secondary electrode can also cause a reduction of the potential difference $V_{12}$, particularly in a case where the reference elements are configured differently from each other and have significantly different initial potentials $V_1$ and $V_2$. In this case, the first step change would lead to smaller values of the absolute amount $|V_{12}|$ of the potential difference and would therefore cause the absolute amount $|V_{12}|$ to fall below the lower tolerance limit $V_u$.

Figure 6:
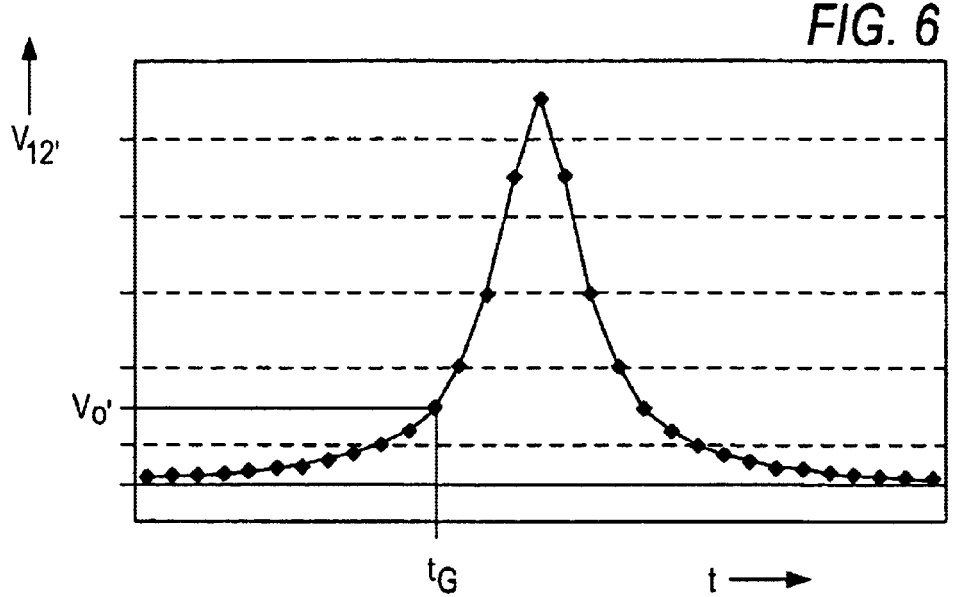
FIG. 6 represents an example for the absolute amount of the first time derivative of the potential difference as a function of the elapsed operating time.

As a further possibility, the base time period $t_G$ can be determined by following the first time derivative $dV_{12}/dt$ of the potential difference (hereinafter referred to as $V_{12}'$). or, more specifically, its absolute amount $|V_{12}'|$. As the first time derivative represents the rate of change of a function, the value of the first time derivative is substantially zero as long as the function stays at an approximately constant value. In areas where the function undergoes a step change, the first time derivative passes through a maximum or minimum. The absolute value of the first time derivative will in this case peak at a maximum value, independent of whether the step change represents an increase or decrease in the value of the function. FIG. 6 represents a time graph of the absolute amount $|V_{12}'|$ of the first time derivative of the potential difference $V_{12}$, where the peak value of $|V_{12}'|$ corresponds to the steepest part in the area of the step change of the potential difference. The point of violation of the tolerance criterion is appropriately defined as the moment where the absolute amount $|V_{12}'|$ of the first time derivative of the potential difference runs above a predefined tolerance value $V_o'$. However, the condition for violating the tolerance criterion can also be defined, e.g., by requiring the absolute amount $|V_{12}'|$ of the first time derivative of the potential difference to first rise above a first tolerance value $V_o'$ and to subsequently fall below a second tolerance value $V_u'$.

Figure 7:
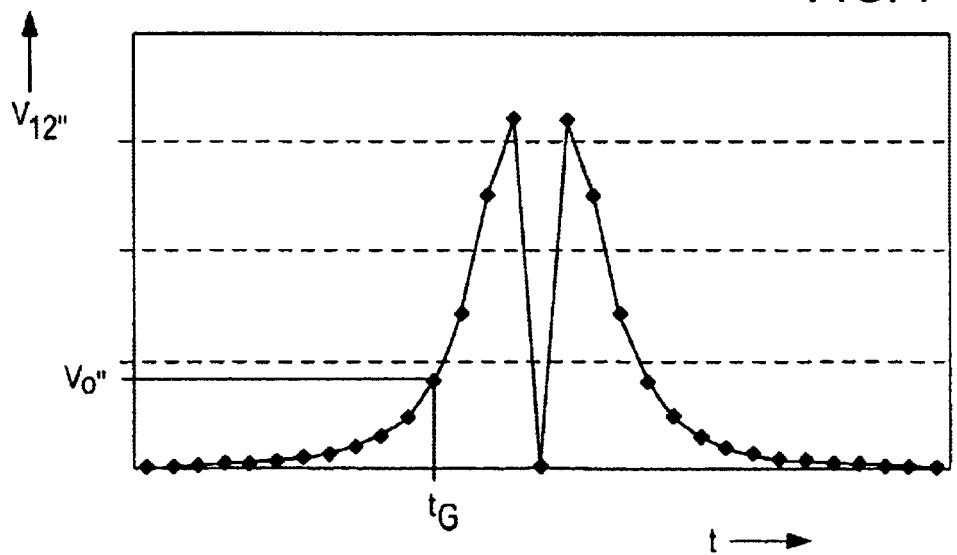
FIG. 7 represents an example for the absolute amount of the second derivative of the potential difference as a function of the elapsed operating time.

It follows directly from the foregoing discussion that one could also work with the absolute amount $|V_{12}''|$ of the second time derivative instead of the absolute amount $|V_{12}'|$ of the first time derivative. FIG. 7 represents a graph of the absolute amount $|V_{12}''|$ of the second time derivative of the potential difference for a time segment around the first step change of the potential difference $V_{12}$. The dip to zero between the two peak values of $|V_{12}''|$ corresponds to the inflection point in the area where the potential difference passes through the step change.

The point of violation of the tolerance criterion is appropriately defined as the moment where the absolute amount $|V_{12}''|$ of the second time derivative of the potential difference runs above a predefined tolerance value $V_o''$. However, as mentioned above, the condition for violating the tolerance criterion can also be defined, e.g., by requiring the absolute amount $|V_{12}''|$ to traverse two or more tolerance values.

In principle, the remaining operating time $\Delta t_R$ could be set independently of the base time period $t_G$, e.g., by using a predefined reference value based on past experience. However, there is a significant advantage in calculating the remaining operating time $\Delta t_R$ as a function of the base time period $t_G$, for example by multiplication with a predefined factor. This offers in particular the opportunity of taking the current operating conditions into account as they could, e.g., cause an exceptionally fast or slow advancement of the frontal boundary of the electrolyte deficiency.

The multiplication factor m needs to be selected so that when the calculated remaining operating time has expired, the front of the electrolyte deficiency has not yet arrived at the primary reference element. As an approximate upper limit for the multiplication factor m, one could use in particular the ratio $L_{21}/L_{o2}$ between the path length $L_{21}$ from the secondary electrode 140 to the primary electrode 122 and the path length $L_{o2}$ from the opening 112 to the secondary electrode 140. The term "path length" in the present context is not necessarily equal to the geometric distance between the respective locations but represents the effective path length traveled by the boundary 148 of the electrolyte-deficient region. As a safety measure, the multiplication factor m should be chosen smaller than the aforementioned path length ratio, for example 90% of the ratio. Of course, this does not preclude a choice of the multiplication factor that is based on past experience.

To guard against a continued use of the measuring probe after failing to notice a change of the potential $V_1$, an additional measure of safety can be achieved by continued monitoring under an alarm criterion after the threshold of the tolerance criterion has been traversed. By setting the remaining operating time to zero when a violation of the alarm criterion has been detected, the operator or the process-control unit can be given a signal that the results delivered by the measuring probe are no longer reliable. The alarm signal can in particular have the form of a message that servicing measures are required immediately. The operational definitions for the alarm criterion can be analogous to those for the tolerance criterion, because it likewise involves the process of detecting a step change of the potential difference $V_{12}$. Consequently, the alarm criterion can again be based on the absolute amount of either the potential difference itself or on the absolute amount of the first or second time derivative of the potential difference.

It is particularly advantageous to monitor the measuring probe under the alarm criterion if the calculation of the remaining operating time $\Delta t_R$ appears doubtful, for example in a case where no reference values from past experience are available for the selection of the multiplication factor m, or if the speed of advancement of the deficiency boundary is variable or unknown because of variable or unknown operating conditions.

The monitoring phase under the alarm criterion is also advantageously used in pre-trial experiments with a given type of measuring probe. In this case, the calculated remaining operating time is ignored and the operation of the measuring probe is continued up to the point where the alarm criterion is actually violated in order to gain reference values for the calculation of the remaining operating time.

The time graphs in FIGS. 4 to 7 are idealized insofar as in certain applications, the signal contains an additional fluctuation or noise component. This unwanted portion of the signal manifests itself even more strongly in the time derivatives, i.e., the signal-to-noise ratio deteriorates progressively with higher-order derivatives. To prevent the risk that a momentary fluctuation of the monitored quantity $|V_{12}|$ or $|V_{12}'|$ or $|V_{12}''|$ could cause a premature violation of the tolerance criterion or alarm criterion, it is appropriate to use signal-filtering in the monitoring of the potential difference. Depending on the measuring principle used in the monitoring process, an analog or digital filtering method can be used.

Clearly, the apparatus according to the invention has useful applications in process-monitoring and/or process-control. By offering a way of preventing the measuring error due to the electrolyte deficiency, the concept of determining the remaining operating time of the potentiometric measuring probe significantly contributes to the safety of a process.

List of Reference Numbers

2 Housing
 4 Enclosed space in 2
 6 Primary reference element
 8 Secondary reference element
 10 Electrolyte
 12 Opening in 2
 14 End portion of 2
 16 Filler mass
 18 Cartridge of 6
 20 Primary electrode
 22 Chlorided silver wire of 20
 24 Primary electrolyte
 26 Open end of 18
 28 Conductor lead for 20
 30 Plug-in contact for 28
 32 Header of 2
 34 Sealing plug of 18
 36 Cartridge of 8
 38 Open end of 36
 40 Secondary electrode
 42 Chlorided silver wire of 40
 44 Secondary electrolyte
 46 Conductor lead for 40
 48 Plug-in contact for 46
 50 Sealing plug of 36
 52 Boundary of electrolyte-deficient region
 54 Electrolyte-deficient region of 16
 56 Non-deficient region of 16
 102 Housing
 104 Enclosed space of 102
 106 Primary reference element
 108, 108*a* Secondary reference element
 110 Electrolyte
 112 Opening of 102
 114 End portion of 102
 116 Filler mass
 118 Interior tube
 120 Open end of 118
 122 Primary electrode
 124 Chlorided silver wire of 122
 126 Primary electrolyte
 128 Chlorided end portion of 124
 130 Closed end of 118
 132 Conductor lead for 122
 134 Header of 102
 136 Seal of 102
 138 Plug-in contact of 132
 140, 140*a* Secondary electrode
 142, 142*a* Chlorided silver wire of 140

144 Conductor lead for 140
146 Plug-in contact for 144
148 Boundary of electrolyte-deficient region
A Longitudinal axis of 2
L Lengthwise offset between 6 and 8
$V_1$ Potential of the primary electrode
$V_2$ Potential of the secondary electrode

What is claimed is:

1. A method of determining a remaining operating time of a potentiometric measuring probe containing an electrolyte, wherein a primary reference element and a secondary reference element are arranged so that an electrolyte deficiency advancing from an opening of the measuring probe arrives at the secondary reference element before it arrives at the primary reference element, the method comprising the steps of:

monitoring a potential difference ($V_{12}$) existing between respective electrical potentials of the primary reference element and the secondary reference element for conformance to a predefined tolerance criterion;

when the tolerance criterion is found to be violated, determining the elapsed operating time from when the measuring probe was put into operation and retaining said elapsed operating time as a base time period ($t_G$);

calculating a remaining operating time ($\Delta t_R$) of the measuring probe from the base time period ($t_G$).

2. The method according to claim 1, wherein a violation of the tolerance criterion causes a warning signal to be triggered.

3. The method according to claim 1, wherein the monitoring of the potential difference ($V_{12}$) is substantially continuous.

4. The method according to claim 1, wherein the monitoring of the potential difference ($V_{12}$) is performed at intermittent points in time.

5. The method according to claim 1, wherein signal-filtering is used in the monitoring of the potential difference ($V_{12}$).

6. The method according to claim 1, wherein a departure of the absolute amount ($|V_{12}|$) of the potential difference from a predefined tolerance range is used as a condition for finding the tolerance criterion violated.

7. The method according to claim 1, wherein a traverse of one or more predefined tolerance values by the absolute amount ($|V_{12}'|$) of the first time derivative of the potential difference is used as a condition for finding the tolerance criterion violated.

8. The method according to claim 1, wherein a traverse of one or more predefined tolerance values by the absolute amount ($|V_{12}''|$) of the second time derivative of the potential difference is used as a condition for finding the tolerance criterion violated.

9. The method according to claim 1, wherein the remaining operating time ($\Delta t_R$) is calculated by multiplying the base time period ($t_G$) with a predefined multiplication factor (m).

10. The method according to claim 1, wherein after a violation of the tolerance criterion has occurred, the potential difference ($V_{12}$) is monitored for conformance to a predefined alarm criterion; and when the alarm criterion is found to be violated, the remaining operating time ($\Delta t_R$) is set to zero.

11. The method according to claim 10, wherein a violation of the alarm criterion causes an alarm signal to be triggered.

12. The method according to claim 10, wherein a departure of the absolute amount ($|V_{12}|$) of the potential difference from a predefined alarm range is used as a condition for finding the alarm criterion violated.

13. The method according to claim 10, wherein a traverse of one or more predefined alarm values by the absolute amount ($|V_{12}'|$) of the first time derivative of the potential difference is used as a condition for finding the alarm criterion violated.

14. The method according to claim 10, wherein a traverse of one or more predefined alarm values by the absolute amount ($|V_{12}''|$) of the second time derivative of the potential difference is used as a condition for finding the alarm criterion violated.

15. Apparatus for determining a remaining operating time of a potentiometric measuring probe, comprising:

a) a potentiometric measuring probe with an electrolyte and with a primary reference element and a secondary reference element that are arranged so that an electrolyte deficiency advancing from an opening of the measuring probe arrives at the secondary reference element before it arrives at the primary reference element;

b) time-measurement means for measuring the elapsed operating time (t) from when the measuring probe was put into operation;

c) monitoring means for monitoring the potential difference ($V_{12}$) existing between the primary reference element and the secondary reference element;

d) calculating means for calculating the remaining operating time ($\Delta t_R$) of the measuring probe.

* * * * *